United States Patent
Pisano et al.

(10) Patent No.: US 7,816,386 B2
(45) Date of Patent: Oct. 19, 2010

(54) CINNAMIC, PHENYLPROPIOLIC AND PHENYLPROPANOIC ACID DERIVATIVES USEFUL AS ANTI-TUMOR AGENTS

(75) Inventors: Claudio Pisano, Aprilia (IT); Gianfranco Battistuzzi, Rome (IT); Maria Di Marzo, Santa Maria a Vico Casera (IT); Giuseppe Giannini, Pomezia (IT); Mauro Marzi, Rome (IT); Loredana Vesci, Rome (IT); Franco Zunino, Milan (IT); Riccardo Pezzi, Morlupo (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 161 days.

(21) Appl. No.: 11/917,039

(22) PCT Filed: May 31, 2006

(86) PCT No.: PCT/EP2006/062790

§ 371 (c)(1),
(2), (4) Date: Feb. 15, 2008

(87) PCT Pub. No.: WO2006/131482

PCT Pub. Date: Dec. 14, 2006

(65) Prior Publication Data

US 2008/0194659 A1    Aug. 14, 2008

(30) Foreign Application Priority Data

Jun. 10, 2005    (EP) .............................. 05012561.6

(51) Int. Cl.
  *A61K 31/42*    (2006.01)
  *A61K 31/165*    (2006.01)
  *A61K 31/404*    (2006.01)
  *C07D 209/04*    (2006.01)
  *C07D 261/06*    (2006.01)
  *C07C 233/01*    (2006.01)

(52) U.S. Cl. .................. 514/378; 514/415; 514/619; 548/240; 548/494; 564/163

(58) Field of Classification Search ............... 564/163
See application file for complete search history.

(56) References Cited

U.S. PATENT DOCUMENTS 3,763,213 A * 10/1973 Heck ..................... 558/376
2003/0032801 A1    2/2003 Lin et al.
2004/0102634 A1    5/2004 Matsuura et al.

FOREIGN PATENT DOCUMENTS

DE    102 25 635 A    12/2003
WO    WO 99/43323 A    9/1999

OTHER PUBLICATIONS

Document No. 139:180089 retrieved from CAPLUS on Jan. 3, 2010.*
Document No. 137:345550 retrieved from CAPLUS on Jan. 3, 2010.*
Document No. 133:309713 retrieved from CAPLUS on Jan. 3, 2010.*
Document No. 133:177112 retrieved from CAPLUS on Jan. 3, 2010.*
Document No. 88:121021 retrieved from CAPLUS on Jan. 3, 2010.*
Document No. 79:146135 retrieved from CAPLUS on Jan. 3, 2010.*

* cited by examiner

*Primary Examiner*—Rebecca L Anderson
*Assistant Examiner*—Shawquia Young
(74) *Attorney, Agent, or Firm*—Lucas & Mercanti, LLP

(57) ABSTRACT

Cinnamic and phenylpropiolic acid derivatives of formula (I) having antitumour and chemo sensitizing activity are described. Also described are pharmaceutical compositions containing the above-mentioned compounds, for the treatment of tumours.

9 Claims, No Drawings

CINNAMIC, PHENYLPROPIOLIC AND PHENYLPROPANOIC ACID DERIVATIVES USEFUL AS ANTI-TUMOR AGENTS

FIELD OF THE INVENTION

The present invention is related to cinnamic and phenylpropiolic and phenylpropanoic acid derivatives having antitumour activity.

BACKGROUND OF THE INVENTION

The therapy of tumours is being currently achieved by surgical intervention, radiation treatment and chemotherapy. The drawbacks of this latter are mainly due to the toxicity of the cytotoxic drugs, which is usually not limited to the cancer cells, and to the acquired resistance of the cancer cells to some of the most widely used drugs, which reduces the long-term efficacy of the therapy.

The elimination of the primary tumour by surgery is not always possible and in any case does not prevent the most metastasizing tumours, such as for example breast cancer or melanoma, to invade other target organs.

It has become evident that the therapy of the metastasizing tumours is unlikely to bring to the complete cure of the patient; therefore, the treatment with cytotoxic drugs is now seen as a palliative and life-prolonging method rather than a curative method. A chronic treatment with a drug having low toxicity would be preferable, while targeted to the control of the progression of the disease.

During the last years cancer drug development has moved from conventional cytotoxic chemotherapeutics to a more mechanism-based targeted approach towards the common goal of tumour growth arrest. The rapid progress in chromatin research and understanding epigenetic control has supplied a plethora of potential targets for intervention in cancer. Histone deacetylases (HDACs) have been widely implicated in growth and transcriptional control, and inhibition of HDAC activity using small molecules causes apoptosis in tumour cells. Histone deacetylase inhibitors are now known to be potent inducers of growth arrest, differentiation, or apoptotic cell death in a variety of transformed cells in culture and in tumour bearing animals (Marks, P. A., Current Opinions in Oncology, 2001, Nov. 13 (6): 477-83; Marks, P., Nat. Rev. Cancer 2001 Dec. 1 (3):194-202).

On the other hand, as anticipated before, another very important and keenly perceived aspect of oncological therapy is the onset of resistance to the drug used by the tumour cells treated. The cells that develop resistance to a drug are often capable of resisting the effects of many other antitumour drugs, even if these are unrelated chemically or act with different mechanisms of action. This type of resistance is called multidrug resistance (MDR) (Annu. Rev. Med 1991, 42: 277-286; Drugs of the Future 1997, 22: 653-660).

A number of tumours, such as, for instance, tumours of the adrenal cortex, colon, kidneys and jejunum and liver carcinoma manifest drug resistance right from the very start of treatment with antitumour drugs (Barrows, L. R. Anti-neoplastic and Immunoactive Drugs, 1995; 75; 1236-1262).

In other cases, the tumour cells acquire resistance in a manner similar to that of bacterial resistance to antibiotics. This type of resistance is based on genetic changes that occur in the tumour cells during treatment; these changes allow the daughter cells to proliferate in a milieu in which the antitumour agent is present.

Whatever the cause of the resistance, it leads to inefficacy of the anti-neoplastic treatment in the long term.

A number of studies suggest that a common form of drug resistance in human tumours derives from the presence of glycoprotein P (Ann. Med. Interna 1997 March; 14 (3): 145-53; Acta Scient Venez. 2000; 51 (1): 45-52). This glycoprotein acts as an energy-dependent membrane pump which expels the antitumour drug from the interior of the cell, thus reducing the cellular concentration of the drug.

Chemosensitisers are compounds that bring about changes in tumour cells or in the body and favour an increase in the therapeutic efficacy of the antitumour agents used.

Chemosensitisers known to be capable of modulating the function of glycoprotein P include calcium-channel blockers (verapamil), calmodulin inhibitors (trifluoperazine), indole alkaloids (reserpine), lysosomotropic agents (chloroquin), steroids, (progesterone), triparanol analogues (tamoxifen), detergents (cremophor EL), and cyclic peptide antibiotics (cyclosporins) (Cancer, Principles & Practice of Oncology, 1993; 4th ed., J. B. Lippincott Co., Philadelphia, Pa., 2661-2664).

DESCRIPTION OF THE INVENTION

We have found that a class of cinnamic, phenylpropiolic and phenylpropanoic acid derivatives possess the requisites essential for such antitumour, anti-metastatic and chemosensitizing activity.

Therefore the main object of the present invention are the compounds of Formula (I) below, which are useful agents as antitumour, anti-metastatic and chemosensitiser agents.

The invention concerns compounds of Formula (I):

[FORMULA I]

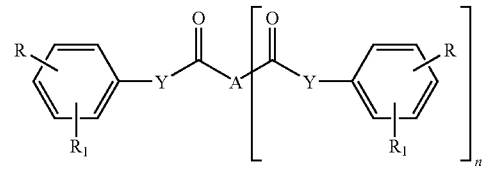

wherein:

n is either 0 or 1;

when n is 0, A is a monovalent group and is selected from the group consisting of: OH, NH—OG, the group

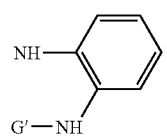

where G and G' are the same or different and are H, glycosyl or acetyl;

when n is 1, A is a divalent group selected from the group consisting of: NH—S—S—NH and $CH_2$—S—S—$CH_2$;

Y is a group selected among HC=CH, FC=CF, FC=CH, CH=CF, $CH_2$—$CH_2$ and C≡C;

R is the group:

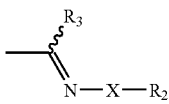

where X is either O, NH;

R is the group:

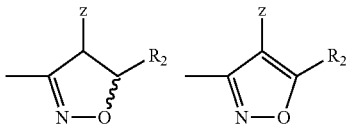

Z selected from the group consisting of:
- H;
- $(C_6-C_{12})$ aryl or $(C_6-C_{12})$ aryl substituted with nitro, halogen, $(C_1-C_4)$ alkoxycarbonyl, hydroxyl or amino;
- $(C_1-C_4)$ alkyl, $(C_2-C_4)$ alkenyl, $(C_2-C_4)$ alkynyl;
- $(C_6-C_{12})$ aryl-$(CH_2)_{n'}$, where aryl is substituted with nitro halogen, $(C_1-C_4)$ alkoxycarbonyl, hydroxyl or amino; where n'=0-3;
- $(C_6-C_{12})$ aryl-CO, where aryl is substituted with nitro halogen $(C_1-C_4)$ alkoxycarbonyl, hydroxy, amino; and
- $(C_3-C_6)$ heterocyclyl-$(C_1-C_4)$ alkyl where at least one of the $CH_2$ of the heterocycle is substituted by O, S, NH;

$R_1$ is selected from the group consisting of:
- H;
- $NH_2$;
- $(C_1-C_4)$ alkyl, $(C_2-C_4)$ alkenyl, $(C_2-C_4)$ alkynyl;
- NH—$(C_2-C_4)$ alkynyl;
- $NO_2$;
- $(C_2-C_4)$ alkynyl;
- halogen;
- $(C_6-C_{12})$ aryl;
- $(C_6-C_{12})$ aryl-$(C_2-C_4)$ alkynylene; and
- $(C_3-C_6)$ heterocyclyl-$(C_2-C_4)$ alkynylene where at least one of the $CH_2$ of the heterocycle is substituted by O, S, NH;

or:

R and $R_1$, taken together with the aromatic group, form a polycyclic group having the following formula:

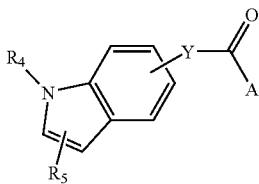

$R_2$ is selected from the group consisting of:
- H;
- $(C_6-C_{12})$ aryl or $(C_6-C_{12})$ aryl substituted with nitro, halogen, $(C_1-C_4)$ alkoxycarbonyl, hydroxyl or amino;
- $(C_1-C_4)$ alkyl, $(C_2-C_4)$ alkenyl, $(C_2-C_4)$ alkynyl;
- $(C_6-C_{12})$ aryl-$(CH_2)_{n''}$, where aryl is substituted with nitro halogen, $(C_1-C_4)$ alkoxycarbonyl, hydroxyl or amino, where n''=0-3;
- $(C_6-C_{12})$ aryl-CO, where aryl is substituted with nitro halogen $(C_1-C_4)$; alkoxycarbonyl, hydroxy, amino; and
- $(C_3-C_6)$ heterocyclyl-$(C_1-C_3)$ alkylene where at least one of the $CH_2$ of the heterocycle is substituted by O, S, NH;

$R_3$ is selected from the group consisting of:
- H;
- $(C_1-C_4)$ alkyl, $(C_2-C_4)$ alkenyl;
- $(C_1-C_4)$ alkyl-NH;
- $(C_1-C_4)$-alkyl-$(C_3-C_6)$-heterocyclylene, where at least one of the $CH_2$ of the heterocycle is substituted by O, S, NH;
- $(C_6-C_{12})$ aryl; and
- $(C_3-C_6)$ heteroaryl where at least one of the CH of the heterocycle is substituted by O, S, NH;

$R_4$ is selected from the group consisting of:
- H;
- $(C_1-C_4)$ alkyl;
- $(C_6-C_{12})$ aryl;
- $(C_6-C_{12})$ aryl-$(C_1-C_4)$ alkynylene;
- $(C_2-C_4)$ alkanoyl; and
- $(C_6-C_{12})$ aryl-CO;

$R_5$ is selected from the group consisting of:
- H;
- linear or branched $(C_1-C_4)$ alkyl;
- linear or branched $(C_2-C_4)$ alkenyl; and
- $OR_6$, where $R_6$ is H, $(C_1-C_4)$ alkyl, mesyl, tosyl, $(C_1-C_4)$ alkanoyl.

The present invention also comprises tautomers, geometrical isomers, optically active forms as enantiomers, diastereomers and racemate forms, as well as pharmaceutically acceptable salts of the compounds of Formula (I).

Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and paratoluenesulfonate salts.

Within the framework of the present invention, examples of the linear or branched $(C_1-C_4)$ alkyl group, are understood to include methyl, ethyl, propyl and butyl and their possible isomers, such as, for example, isopropyl, isobutyl, and ter-butyl.

Examples of the linear or branched $(C_2-C_4)$ alkenyl group are methylidene, ethylidene, vinyl, allyl, propargyl, and butylene, where the double carbon-carbon bond may be situated in the various possible positions of the alkylene chain, which can also be branched in the context of the isomery allowed.

Examples of the $(C_6-C_{12})$ aryl or $(C_6-C_{12})$ aryl-$(C_1-C_4)$ alkyl group are phenyl, 1- or 2-naphthyl, anthracenyl, benzyl, 2-phenylethyl 1-phenylethyl, 3-phenylpropyl, 2-anthracenylpropyl, 1-anthracenylpropyl, naphthylmethyl, 2-naphthylethyl, 1-naphthylethyl, 3-naphthylpropyl, 2-naphthylpropyl, 1-naphthylpropyl.

As used herein, the term "$(C_3-C_6)$ heterocyclo" or the term "$(C_3-C_6)$ heterocyclyl" refers to a monovalent three to six-membered non-aromatic ring containing one or more heteroatomic substitutions independently selected from S, O, or N and having zero to five degrees of unsaturation. Examples of "heterocyclic" as used herein include, but are not limited to, tetrahydrofuryl, pyranyl, 1,4-dioxanyl, 1,3-dioxanyl, piperidinyl, pyrrolidinyl, tetrahydrothiopyranyl, tetrahydrothiophenyl, and the like.

As used herein, the term "$(C_3-C_6)$ heterocyclylene" refers to a divalent three to six membered non-aromatic heterocyclic ring radical containing one or more heteroatoms independently selected from S, O, or N and having zero to five degrees of unsaturation. Examples of "heterocyclylene" as used herein include, but are not limited to, tetrahydrofuran-2,5-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, and the like.

What is meant by halogen is fluorine, chlorine, bromine and iodine.

Examples of the glycosyl residue are 6-D-galactosyl and 6-D-glucosyl.

According to independently preferred embodiments of the invention, A is OH or NH-OG, where G is H; Y is the group HC=CH; $R_1$, $R_3$, $R_4$ and $R_5$ are H; and $R_2$ is selected from the group consisting of: $R_2$ is selected from the group consisting of: H; $C_6-C_{11}$ aryl; $C_6-C_{11}$ aryl$(CH_2)_n$ where aryl is substituted with nitro, halogen, $C_1-C_4$ alkoxycarbonyl; $C_6-C_{11}$ aryl-CO, $C_2-C_4$ heterocycle-alkyl where at least one of the $CH_2$ of the heterocycle is substituted by NH; and n is 2.

In particular compounds of Formula (I) may exist as cis- (Z-) o trans (E-) isomer with respect to the position of $R_3$. All these compounds are included in the present invention.

Moreover, depending on the meaning of the group Y the compounds of the present invention may exist as diastereoisomers (cis or trans, E or Z) or mixtures thereof. All these compounds are included in the present invention.

The following are some of the most preferred compounds according to the invention:
(2E)-N-hydroxy-3-(4-{[(allyloxy)imino]methyl}phenyl)acrylamide (ST2984);
(2E)-N-hydroxy-3-{4-[(phenoxyimino)methyl]phenyl}acrylamide (ST2985);
(2E)-N-hydroxy-3-[4-({[(4-nitrobenzyl)oxy]imino}-methyl)phenyl]acryl-amide (ST2987);
(2E)-N-hydroxy-3-{4-[(hydroxyimino)methyl]phenyl}acrylamide (ST2983);
(2E)-N-hydroxy-3-[4-({[(pentafluorobenzyl)oxy]imino}-methyl)phenyl]-acryl-amide (ST2986);
(2E)-N-hydroxy-3-[4-({[(4-methoxycarbonylbenzoyl)oxy]imino}-methyl)phenyl]-acrylamide (ST3049);
(2E)-N-hydroxy-3-{4-[(2-morpholin-4-ylethoxyimino)methyl]-phenyl}-acryl-amide (ST3050);
(2E)-3-(4-{[(benzyloxy)imino]methyl}phenyl)-N-hydroxyacrylamide (ST2840);
(2E)-N-hydroxy-3-(4-{[(4-chlorobenzoyl)hydrazono]-methyl}phenyl)acryl-amide (ST2888);
(2E)-N-(2-aminophenyl)-3-[4-({[(4-nitrobenzyl)oxy]imino}-methyl)phenyl]-acrylamide (ST3070);
(2E)-N-hydroxy-3-(1H-indol-5-yl)acrylamide (ST2880);
(2E)-3-[4-({[(4-nitrobenzyl)oxy]imino}methyl)phenyl]acrylic acid (ST3075);
(2E)-3-(4-{[(benzyloxy)imino]methyl}phenyl)acrylic acid (ST3076);
(2E)-N-hydroxy-3-{3-[(2-morpholin-4-ylethoxyimino)methyl]-phenyl}-acryl-amide hydrochloride (ST3576);
N-hydroxy-3-[4-({[(4-nitrobenzyl)oxy]imino}-methyl)phenyl]propanamide (ST3330);
N-hydroxy-3-{4-[(E)-{[(4-nitrobenzyl)oxy]imino}methyl]phenyl}prop-2-ynamide (ST3618); 2E)-N-(2-Amino-phenyl)-3-{4-[(2-morpholin-4-yl-ethoxyimino)methyl]-phenyl}-acrylamide hydrochloride (ST3573) and
(2E)-N-Mercapto-3-{4-[(4-nitro-benzyloxyimino)-methyl]-phenyl}-acryl-amide (ST3605).

The experimental results obtained (reported in the section entitled "Examples") show that the compounds of Formula (I), both alone and in combination with other known antitumour drugs, are useful agents for the treatment of tumours.

A further object of the invention described herein are compounds with general Formula (I) and their use in the medical field.

A further object of the invention described herein is a pharmaceutical composition containing as active ingredient a compound of Formula (I) and at least a pharmaceutically acceptable excipient and/or diluent.

A further object of the invention described herein are compounds with general Formula (I) and a process for their preparation.

A further object of the invention described herein is a pharmaceutical composition containing as active ingredient a compound of Formula (I), for the treatment of a tumour pathology, in which the tumour is selected from the group consisting of sarcoma, carcinoma, carcinoid, bone tumour, neuroendocrine tumour, lymphoid leukaemia, acute promyelocytic leukaemia, myeloid leukemia, monocytic leukaemia, megakaryoblastic leukaemia and Hodgkin's disease.

A further object of the invention described herein is a pharmaceutical composition containing as active ingredient a compound Formula (I), for the treatment of a tumour pathology, in which the tumour has shown drug resistance to the previous antibiotics used for its treatment, in which said compound of Formula (I) exerts a chemosensitizing effect on said drug resistant tumour.

A further object of the invention described herein is a pharmaceutical composition containing as active ingredient a compound of Formula (I), in combination with one or more known antitumour agents, in which the antitumour compound is selected from the group consisting of alkylating agents, topoisomerase inhibitors, anti-tubulin agents, intercalating compounds, anti-metabolites, natural products such as vinca alkaloids, epipodophyllotoxins, antibiotics, enzymes, taxans, and cytodifferentiating compounds.

Among the cytodifferentiating antitumour agents the one preferred is all-trans retinoic acid.

Another object of the present invention is a process for preparing any of the pharmaceutical compositions as mentioned above, comprising mixing the compound(s) of Formula (I) with suitable excipient and/or diluent.

A further object of the invention described herein is the use of a compound of Formula (I) for the preparation of a medicine for the treatment of a tumour pathology.

A further object of the invention described herein is the use of a compound of Formula (I) for the preparation of a medicine for the treatment of a tumour pathology in which the tumour has shown drug resistance to the previous antitumour drugs used for its treatment, in which said compound of Formula (I) exerts a chemosensitizing effect on said drug-resistant tumour.

A further object of the invention described herein is the use of a compound of Formula (I), in combination with one or more known antitumour agents, for the preparation of a medicine for the treatment of tumour pathologies.

A further object of the invention described herein is the use of a compound of Formula (I) in combination with all-trans retinoic acid for the preparation of a medicine for the treatment of acute promyelocytic leukaemia.

Another object of the invention is a method of treating a mammal suffering from a tumour pathology, comprising administering a therapeutically effective amount of the compound(s) of Formula (I).

"Therapeutically effective amount" is an amount effective to achieve the medically desirable result in the treated subject. The pharmaceutical compositions may contain suitable pharmaceutical acceptable carriers, biologically compatible vehicles suitable for administration to an animal (for example, physiological saline) and eventually comprising auxiliaries (like excipients, stabilizers or diluents) which facilitate the processing of the active compounds into preparations which can be used pharmaceutical.

The pharmaceutical compositions may be formulated in any acceptable way to meet the needs of the mode of administration. The use of biomaterials and other polymers for drug delivery, as well the different techniques and models to validate a specific mode of administration, are disclosed in literature.

Modifications of the compounds of the invention to improve penetration of the blood-brain barrier would also be useful.

Any accepted mode of administration can be used and determined by those skilled in the art. For example, administration may be by various parenteral routes such as subcutaneous, intravenous, intradermal, intramuscular, intraperitoneal, intranasal, transdermal, oral, or buccal routes.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyloleate or triglycerides.

Aqueous injection suspensions that may contain substances increasing the viscosity of the suspension include, for example, sodium carboxymethyl cellulose, sorbitol, and/or dextran. Optionally, the suspension may also contain stabilizers.

Pharmaceutical compositions include suitable solutions for administration by injection, and contain from about 0.01 to 99 percent, preferably from about 20 to 75 percent of active compound together with the excipient. Compositions which can be administered rectally include suppositories.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight.

The compounds of the present invention may be administered to the patient intravenously in a pharmaceutical acceptable carrier such as physiological saline.

Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal.

As well known in the medical arts, dosages for any one patient depends upon many factors, including the patient's size, body surface area, age, the particular compound to be administered, sex, time and route of administration, general health, and other drugs being administered concurrently.

All references cited herein are entirely incorporated by reference herein, including all data, tables, figures, and text presented in the cited references.

Additionally, the entire contents of the references cited within the references cited herein are also entirely incorporated by reference. Reference to known method steps, conventional method steps, known methods or conventional methods is not in any way an admission that any aspect, description or embodiment of the present invention is disclosed, taught or suggested in the relevant art.

Once understood the features of the methods and products disclosed in present application, the necessity and kind of additional steps can be easily deduced by reviewing prior art, as well as the non-limiting following figures and examples describing the basic details and some applications of the invention The compounds of Formula (I) may be prepared from readily available starting materials using the following general methods and procedures. It will be appreciated that where typical or preferred experimental conditions (i.e. reaction temperatures, time, moles of reagents, solvents, etc.) are given, other experimental conditions can also be used, unless otherwise stated. Optimum reaction conditions may vary with the particular reactants or solvents used, but such conditions can be determined by one skilled in the art by routine optimisation procedures.

A process for preparing the compounds of the present invention comprises reacting a 4-formyl-cinnamic or a 3-(4-formylphenyl)propanoic acid derivative with a hydroxylamine derivative.

The compounds of the present invention can be prepared for example according to the following general schemes.

GENERAL SCHEME I

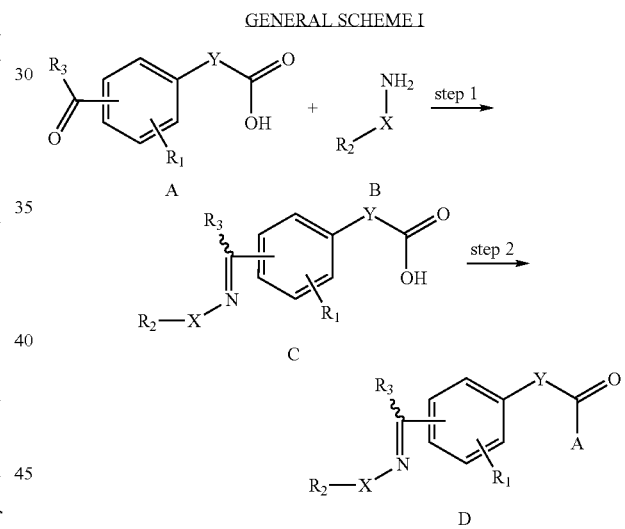

Step 1 is carried out dissolving A, i.e. 4-formyl-cinnamic acid or 4-formyl-cinnamic acid $R_1$ substituted (Y=CH=CH, $R_3$=H,), 3-(4-formylphenyl)prop-2-ynoic acid or 3-(4-formylphenyl)prop-2-ynoic acid $R_1$ substituted (Y=C=C, R3=H), 3-(4-formylphenyl)propanoic acid or 3-(4-formylphenyl)propanoic acid $R_1$ substituted (Y=CH$_2$—CH$_2$, $R_3$=H) in organic solvents, i.e. DMF, DMA, DMSO, together with B, i.e. hydroxylamines (X=O) or their hydrochloride salts or hydrazines (X=NH) substituted. The mixture is kept under stirring at temperatures ranging from 20° C. to 70° C. Compounds C are obtained as crude products.

Step 2 can be carried out as described in one the following papers:

Bauer, L.; Exner, O. *Angew. Chem. Int. Edit* 1974, 13, 376;

Remiszewski, S. W.; Sambucetti, L. C.; Atadja, P.; Bair, K. W.; Cornell, W. D. Green, M. A.; Howell, K. L.; Jung, M.; Kwon, P.; Trogani, N.; Walker, H. *J. Med. Chem.* 2002, 45, 753;

Mai, A.; Massa, S.; Ragno, R.; Cerbara, I.; Jesacher, F.; Loidl, P.; Brosch, G. *J. Med. Chem.* 2003, 46, 512;

Giacomelli, G.; Porcheddu, A.; Salaris, M. *Org. Lett.* 2003, 5, 2715;

Sakamoto, T.; Kikugawa, Y. *J. Org. Chem.* 1994, 59, 929; and

Barta, T. E. et al. *Bioorg. Med. Chem. Lett.* 2000, 10, 2815.

In particular Step 2 is carried out in organic solvents, i.e. DMF, DMA, DMSO, mixing compounds C with a condensing agent [i.e. EDC Hydrochloride, HATU, PyBOP, HOBt] and a base as DIEA, TEA. Nucleophilic nitrogen species as hydroxylamine, o-phenylendiamine are added at the mixture under stirring at temperatures ranging from 20° C. to 60° C. Compounds D are purified by crystallization or by chromatographic method.

In the case in which R and $R_1$ taken together with the aromatic group form a polycyclic group, the compounds of the present invention can be prepared according to the following Scheme II:

DIEA, TEA. Nucleophilic nitrogen species as hydroxylamine, o-phenylendiamine are added to the mixture under stirring at temperatures ranging from 20° C. to 60° C. Compounds F (Y=CH=CH, or C≡C or $CH_2$—$CH_2$, A=CONHOH) are purified by crystallization from $CH_2Cl_2$ or by chromatographic method.

The following examples further illustrate the invention without limiting its scope.

GENERAL SCHEME III

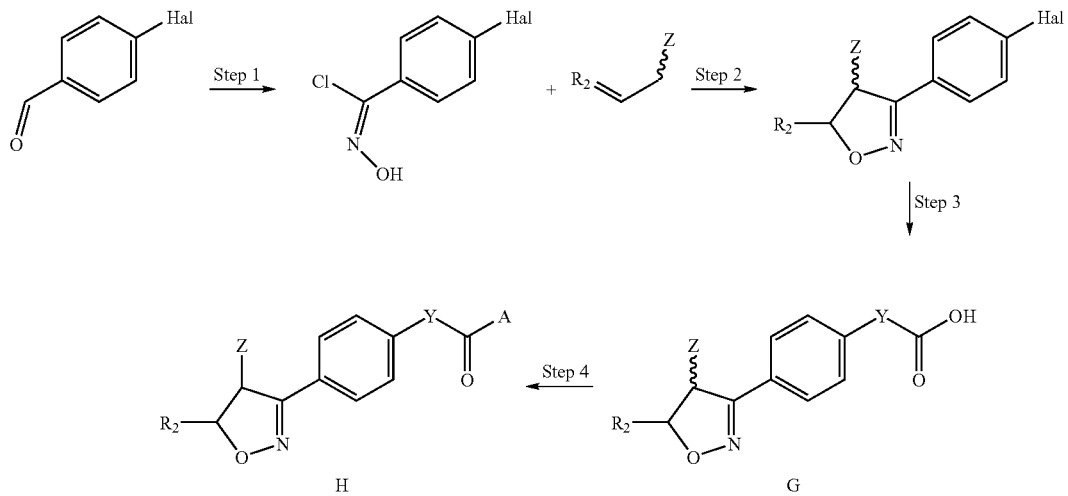

General Conditions for Scheme III

Step 1 is carried out dissolving 4-halogen-benzaldehyde, i.e. 4-Iodo-benzaldehyde in organic solvents, i.e. EtOH, MeOH, i-PrOH, together with $NH_2OH$. The mixture is kept under stirring at temperatures ranging from 20° C. to 70° C. The compound obtained as crude product was added to a organic solvents i.e. DCM, DMF, DMA, DMSO or mixture with NCS, to obtained the desiderated hydroximinoyl chloride.

Step 2 in situ conversion of hydroximinoyl chloride to the corresponding nitrile oxide was carried in organic solvents i.e. $CH_2Cl_2$, and a base as DBU, DIEA, TEA followed by cycloaddition with allyl-derivates Z—CH=CH—$R_2$ as the dipolarophile generated the racemic isoxazoline.

Step 3 the compounds G (Y=CH=CH, C≡C or $CH_2$—$CH_2$) i.e. 4-(racemic-isoxazoline)-cinnamic acid was achieved by basic hydrolysis (NaOH, KOH, Ca(OH)$_2$) of ester-derivates in organic solvents i.e. EtOH, MeOH, i-PrOH, obtained by reaction of opportune acrilates and halogenated-phenyl-isoxazoline via proper Pd-catalysis in presence of opportune base as DBU, DIEA, TEA in organic solvents i.e. THF, DMF, DMA, DMSO or mixture.

Step 4 The reaction is carried out in organic solvents i.e. DCM, DMF, DMA, DMSO or mixture, mixing compounds G (Y=CH=CH, C≡C or $CH_2$—$CH_2$) with a condensing agent [i.e. EDC, HATU, PyBOP, HOBt] and a base as DBU, DIEA, TEA. Nucleophilic nitrogen species as hydroxylamine, o-phenylendiamine are added to the mixture under stirring at temperatures ranging from 20° C. to 60° C. Compounds H(Y=CH=CH, C≡C or $CH_2$—$CH_2$, A=CONHOH) are purified by crystallization from $CH_2Cl_2$ or by chromatographic method.

GENERAL SCHEME II

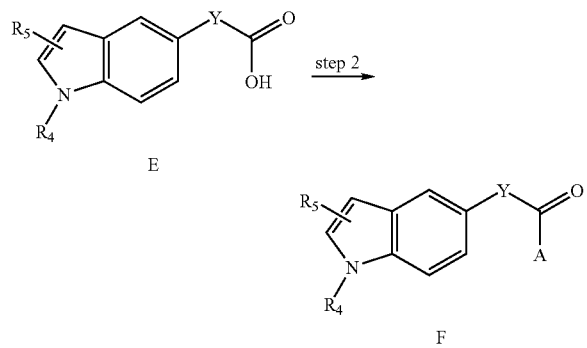

General Conditions for Scheme II

The reaction is carried out in organic solvents i.e. DCM, DMF, DMA, DMSO or mixture, mixing compounds E (Y=CH=CH, or C≡C, or $CH_2$—$CH_2$,) with a condensing agent [i.e. EDC, HATU, PyBOP, HOBt] and a base as DBU,

GENERAL SCHEME IV

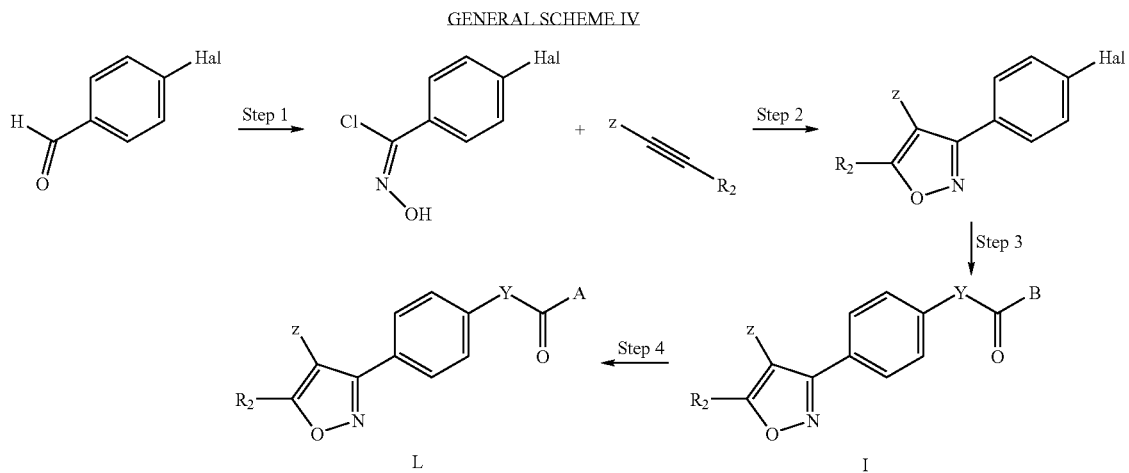

General Conditions for Scheme IV

Step 1 is carried out dissolving 4-halogen-benzaldehyde, i.e. 4-Iodo-benzaldehyde in organic solvents, i.e. EtOH, MeOH, i-PrOH, together with $NH_2OH$. The mixture is kept under stirring at temperatures ranging from 20° C. to 70° C. The compound obtained as crude product was added to a organic solvents i.e. DCM, DMF, DMA, DMSO or mixture with NCS, to obtained the desiderated hydroximinoyl chloride.

Step 2 in situ conversion of hydroximinoyl chloride to the corresponding nitrile oxide was carried in organic solvents i.e. $CH_2Cl_2$, and a base as DBU, DIEA, TEA followed by cycloaddition with propargyl-derivates Z—C≡C—$R_2$ as the dipolarophile generated the racemic isoxazoline.

Step 3 the compounds I (Y=CH=CH, C≡C or $CH_2$—$CH_2$) i.e. 4-(racemic-isoxazoline)-cinnamic acid was achieved by basic hydrolysis (NaOH, KOH, Ca(OH)$_2$) of ester-derivatives in organic solvents i.e. EtOH, MeOH, i-PrOH, obtained by reaction of opportune acrilates and halogenated-phenyl-isoxazoline via proper Pd-catalysis in presence of opportune base as DBU, DIEA, TEA in organic solvents i.e. THF, DMF, DMA, DMSO or mixture.

Step 4 The reaction is carried out in organic solvents i.e. DCM, DMF, DMA, DMSO or mixture, mixing compounds I (Y=CH=CH, C≡C or $CH_2$—$CH_2$) with a condensing agent [i.e. EDC, HATU, PyBOP, HOBt] and a base as DBU, DIEA, TEA. Nucleophilic nitrogen species as hydroxylamine, O-phenylendiamine are added to the mixture under stirring at temperatures ranging from 20° C. to 60° C. Compounds L (Y=CH=CH, C≡C or $CH_2$—$CH_2$, A=CONHOH) are purified by crystallization from $CH_2Cl_2$ or by chromatographic method.

The following examples further illustrate the invention without limiting its scope.

EXAMPLES

Example 1

Preparation of (2E)-N-hydroxy-3-(4-{[(allyloxy) imino]methyl}phenyl)acrylamide (ST2984)

Step 1: a solution of trans 4-formyl-cinnamic acid A (Y=CH=CH, $R_1$, =H, $R_3$=H, 0.346 g, 1.96 mmol.) and B O-Allylhydroxylamine hydrochloride (0.258 g, 2.37 mmol.) dissolved in 2 mL of DMF was warmed at 50° C. and stirred for 5 h. Then the solution was diluted with AcOEt and washed with water. Organic layer was dried on $Na_2SO_4$ and then concentrated under reduced pressure to give 0.421 g of the intermediate C (2E)-3-(4-{[(benzyloxy)imino]methyl}phenyl)acrylic acid (93% yield).

MS (ESI) m/z: [M−1]⁻=230.3

Step 2: in a flask intermediate C obtained from step 1 (0.123 g, 0.53 mmol) was dissolved in 1.5 mL of DMF together with HATU (0.222 g, 0.58 mmol) and DIEA (185 µL, 1.06 mmol). After 0.5 h, a solution of hydroxylamine as hydrochloride salt (0.055 g, 0.80 mmol) and DIEA (139 µL, 0.80 mmol) in 1.5 mL of DMF was added. The mixture was stirred at room temperature for 24 h and then diluted with a HCl solution (pH=3.5). The precipitate was recovered by filtration and then crystallized by $CH_2Cl_2$ to give 0.088 g of D (ST2984, 40% yield).

MS (ESI) m/z: [M−1]⁻=245.0
[M+23]⁺=269.0

¹H-NMR (200 MHz, DMSO-d6) δ (ppm): 4.55-4.75 (d, J=5 Hz, 2H, $CH_2$), 5.20-5.40 (dd, $J_{trans}$=17.6 Hz, $J_{cis}$=10.6 Hz, 2×CH), 5.9-6.1 (m, 1H, CH), 6.4-6.6 (d, J=15.8 Hz, 1H, CH), 7.4-7.6 (d, J=15.4 Hz, 1H, CH), 7.6 (bs, 4H, 4×$CH_{ar}$), 8.2 (s, 1H, CH), 9.1 (bs, 1H, NH), 10.8 (bs, 1H, OH).

¹³C-NMR (50 MHz, DMSO-d6) δ (ppm): 75.3, 118.6, 120.7, 128.1, 128.7, 133.5, 135.1, 137.0, 138.3, 149.3, 163.3.

Example 2

Preparation of (2E)-N-hydroxy-3-{4-[(phenoxyimino)methyl]phenyl}acrylamide (ST2985)

Step 1: intermediate C (2E)-3-{4-[(phenoxyimino)methyl]phenyl}acrylic acid for the synthesis of ST2985 was obtained (0.520 g, 99% yield) as described in step 1, example 1, starting from trans 4-formyl-cinnamic acid A (0.342 g, 1.94 mmol) and B O-Phenylhydroxylamine hydrochloride (0.339 g, 2.33 mmol).

MS (ESI) m/z: [M−1]⁻=266.4

Step 2: compound ST2985 was obtained (0.100 g, 48% yield) as described in step 2, example 1, starting from intermediate C (0.201 g, 0.75 mmol).

MS (ESI) m/z: [M−1]⁻=281.1
[M+23]⁺=305.0

¹H-NMR (200 MHz, DMSO-d6) δ (ppm): 6.5-6.7 (d, J=15.7 Hz, 1H, CH), 7.0-7.1 (t, J=6.9 Hz, 1H, $CH_{ar}$), 7.2-7.3 (d, J=8.0 Hz, 2H, $2 \times CH_{ar}$), 7.3-7.4 (t, J=7.3 Hz, 2H, $2 \times CH_{ar}$), 7.4-7.6 (d, J=16.1 Hz, 1H, CH), 7.6-7.7 (d, J=7.7 Hz, 2H, $2 \times CH_{ar}$), 7.8-7.9 (d, J=7.7 Hz, 2H, $2 \times CH_{ar}$), 8.7 (s, 1H, CH), 9.1 (bs, 1H, NH), 10.8 (bs, 1H, OH).

¹³C-NMR (50 MHz, DMSO-d6) δ (ppm): 115.0, 121.3, 123.2, 128.8, 128.9, 130.3, 132.6, 137.9, 138.2, 152.8, 159.6, 163.2.

Example 3

Preparation of (2E)-N-hydroxy-3-[4-({[(4-nitrobenzyl)oxy]imino}-methyl)phenyl]acrylamide (ST2987)

Step 1: intermediate C (2E)-3-[4-({[(4-nitrobenzyl)oxy]imino}-methyl)phenyl]acrylic acid (ST3075) for the synthesis of ST2987 was obtained (0.610 g, 94% yield) as described in step 1, example 1, starting from trans 4-formyl-cinnamic acid A (0.348 g, 1.97 mmol) and B O-(4-Nitrobenzyl)hydroxylamine hydrochloride (0.485 g, 2.37 mmol).

MS (ESI) m/z: $[M-1]^-$=325.3

¹H-NMR (200 MHz, DMSO-d6) δ (ppm): 5.34 (s, 2H, $CH_2$), 6.5-6.7 (d, J=15.7 Hz, 1H, CH), 7.5-7.8 (m, 7H, $6 \times CH_{ar}$, CH), 8.2-8.3 (d, J=8.4 Hz, 2H, $2 \times CH_{ar}$), 8.41 (s, 1H, CH), 12.4 (bs, 1H, OH).

¹³C-NMR (50 MHz, DMSO-d6, δ): 75.0, 121.0, 124.3, 128.1, 129.4, 129.5, 133.8, 136.7, 143.7, 146.5, 147.7, 150.3, 168.2.

Step 2: compound ST2987 was obtained (0.120 g, 44% Yield) as described in step 2, example 1, starting from intermediate C (0.262 g, 0.80 mmol).

MS (ESI) m/z: $[M-1]^-$=340.2
$[M+23]^+$=364.4

¹H-NMR (200 MHz, DMSO-d6) δ (ppm): 5.34 (s, 2H, $CH_2$), 6.4-6.6 (d, J=15.6 Hz, 1H, CH), 7.4-7.6 (d, J=15.8 Hz, 1H, CH), 7.62 (bs, 4H, $4 \times CH_{ar}$), 7.6-7.7 (d, J=8.4 Hz, 2H, $2 \times CH_{ar}$), 8.2-8.3 (d, J=8.4 Hz, 2H, $2 \times CH_{ar}$), 8.41 (s, 1H, CH), 9.09 (bs, 1H, NH), 10.80 (bs, 1H, OH).

¹³C-NMR (50 MHz, DMSO-d6) δ(ppm): 74.9, 120.9, 124.3, 128.2, 128.7, 129.5, 133.1, 137.3, 138.2, 146.5, 147.8, 150.4, 163.2.

Example 4

Preparation of (2E)-N-hydroxy-3-{4-[(hydroxyimino)methyl]phenyl}acrylamide (ST2983)

Step 1: intermediate C (2E)-3-{4-[(hydroxyimino)methyl]phenyl}acrylic acid for the synthesis of ST2983 was obtained (0.355 g, 93%) as described in step 1, example 1, starting from trans 4-formyl-cinnamic acid A (0.352 g, 2.00 mmol) and B Hydroxylamine hydrochloride (0.167 g, 2.40 mmol).

MS (ESI) m/z: $[M-1]^-$=190.2

Step 2: compound ST2983 was obtained (0.060 g, 40%) as described in step 2, example 1, starting from intermediate C (0.075 g, 0.39 mmol) except for work-up and purification: reaction mixture was concentrated under reduced pressure and crude product was purified by preparative RP-HPLC (column Lichrosorb RP18 25×2.5 mmID, eluent $H_2O$/$CH_3CN$=50/50+$CH_3COONH_4$ 50 mM, flow 10 mL/min).

MS (ESI) m/z: $[M-1]^-$=205.3
$[M+23]^+$=229.2

¹H-NMR (200 MHz, DMSO-d6) δ (ppm): 6.4-6.6 (d, J=15.8 Hz, 1H, CH), 7.4-7.6 (d, J=15.8 Hz, 1H, CH), 7.61 (bs, 4H, $4 \times CH_{ar}$), 8.15 (s, 1H, CH), 9.09 (bs, 1H, NH), 10.79 (bs, 1H, OH), 11.37 (bs, 1H, OH).

Example 5

Preparation of (2E)-N-hydroxy-3-[4-({[(pentafluorobenzyl)oxy]imino}-methyl)phenyl]-acryl-amide (ST2986)

Step 1: intermediate C (2E)-3-[4-({[(pentafluorobenzyl)oxy]imino}-methyl)phenyl]acrylic acid for the synthesis of ST2986 was obtained (0.710 g, 97% yield) as described in step 1, example 1, starting from trans 4-formyl-cinnamic acid A (0.346 g, 1.96 mmol) and B O-(2,3,4,5,6-Pentafluorobenzyl)hydroxylamine hydrochloride (0.588.2 g, 2.35 mmol).

MS (ESI) m/z: $[M-1]^-$=370.1

Step 2: compound ST2986 was obtained (0.060 g, 50% yield) as described in step 2, example 1, starting from intermediate C (0.115 g, 0.31 mmol).

MS (ESI) m/z: $[M-1]^-$=385.1
$[M+23]^+$=409.0

¹H-NMR (200 MHz, DMSO-d6) δ (ppm): 5.27 (s, 2H, $CH_2$), 6.4-6.6 (d, J=15.7 Hz, 1H, CH), 7.4-7.6 (d, J=15.7 Hz, 1H, CH), 7.60 (bs, 4H, $4 \times CH_{ar}$), 8.90 (s, 1H, CH), 9.08 (bs, 1H, NH), 10.80 (bs, 1H, OH).

¹⁹F-NMR (188 MHz, DMSO-d6) δ (ppm): −138.3 (d, J=23.0 Hz), −149.2 (t, J=21.3 Hz), −158.1 (t, J=22.0 Hz).

Example 6

Preparation of (2E)-N-hydroxy-3-[4-({[(4-methoxycarbonylbenzyl)oxy]imino}-methyl)phenyl]-acrylamide (ST3049)

Step 1: intermediate C (2E)-3-{4-[({[4-(methoxycarbonyl)benzyl]oxy}-imino)methyl]phenyl}acrylic acid for the synthesis of ST3049 was obtained (0.300 g, 80% yield) as described in step 1, example 1, starting from trans 4-formyl-cinnamic acid A (0.197 g, 1.12 mmol) and B O-(4-methoxycarbonylbenzyl)hydroxylamine hydrochloride (0.292 g, 1.34 mmol).

MS (ESI) m/z: $[M-1]^-$=338.2

Step 2: Compound ST3049 was obtained (75 mg, 58% yield) as described in step 2, example 1, starting from intermediate C (0.124 g, 0.36 mmol).

MS (ESI) m/z: $[M-1]^-$=353.2

¹H-NMR (200 MHz, DMSO-d6) δ (ppm): 3.85 (s, 3H, $CH_3$), 5.28 (s, 2H, $CH_2$), 6.5-6.7 (d, J=15.8 Hz, 1H, CH), 7.5-7.7 (m, 5H, $4 \times CH_{ar}$+CH), 7.7-7.8 (d, J=8.0 Hz, 2H, $2 \times CH_{ar}$), 7.9-8.0 (d, J=8.1 Hz, 2H, $2 \times CH_{ar}$), 8.38 (s, 1H, CH), 9.10 (bs, 1H, NH), 10.78 (bs, 1H, OH).

¹³C-NMR (50 MHz, DMSO-d6) δ (ppm): 52.8, 75.5, 120.9, 128.2, 128.7, 128.8, 129.7, 130.0, 133.2, 137.2, 138.2, 144.0, 150.0, 163.2, 166.8.

Example 7

Preparation of (2E)-N-hydroxy-3-{4-[(2-morpholin-4-ylethoxyimino)methyl]-phenyl}-acryl-amide (ST3050)

Step 1: intermediate C (2E)-3-(4-{(E)-[(2-morpholin-4-ylethoxy)imino]methyl}-phenyl)acrylic acid for the synthesis of ST3050 was obtained (0.140 g, 91% yield) as described in step 1, example 1, starting from trans 4-formyl-cinnamic acid A (0.089 g, 0.50 mmol) and B 2-(2-morpholyn-4-yl)-O-ethylhydroxylamine dihydrochloride (0.081 g, 0.55 mmol).

MS (ESI) m/z: $[M+1]^+$=305.2

Step 2: compound ST3050 was obtained (45 mg, 30% yield) as described in step 2, example 1, starting from intermediate C (0.140 g, 0.46 mmol); reaction mixture was worked-up and purified as in example 4

Compound ST3050 as hydrochloride was obtained (1.241 mg, 98% yield) after acid hydrolysis (HCl in THF solution) of (2E)-3-{4-[(2-Morpholin-4-yl-ethoxyimino)-methyl]-phenyl}-N-trityloxy-acrylamide obtained (2.000 g, 3.56 mmol, 67% yield) by reaction of intermediate C (1.800 g, 5.29 mmol) with ethyl chloroformate (607 μL, 6.35 mmol) and TEA (959 μL, 6.88 mmol) in 5 mL of anhydrous THF (according to procedure described in Mai A., Pezzi R. et all. *J. Med. Chem.* 2005, 48, 3344 and in Mai A., Pezzi R. et all. *J. Med. Chem.* 2003, 46, 4826).

MS (ESI) m/z: $[M+1]^+$=320.3

$^1$H-NMR (200 MHz, DMSO-d6) δ (ppm): 2.4-2.5 (t, J=4.4 Hz, 4H, 2×CH$_2$), 2.6-2.7 (t, J=5.9 Hz, 2H, CH$_2$), 3.5-3.6 (t, J=4.4 Hz, 4H, 2×CH$_2$), 4.2-4.3 (t, J=5.9 Hz, 2H, CH$_2$), 6.4-6.6 (d, J=15.8 Hz, 1H, CH), 7.4-7.6 (d, J=16.1 Hz, 1H, CH), 7.62 (bs, 4H, 4×CH$_{ar}$), 8.27 (s, 1H, CH), 9.09 (bs, 1H, NH), 10.79 (bs, 1H, OH).

$^{13}$C-NMR (50 MHz, DMSO-d6) δ (ppm): 54.4, 57.7, 66.9, 72.2, 120.8, 128.1, 128.7, 133.6, 137.0, 138.3, 149.0, 163.2.

Example 8

Preparation of (2E)-3-(4-{[(benzyloxy)imino]methyl}phenyl)-N-hydroxyacrylamide (ST2840)

Step 1. Intermediate C (2E)-3-(4-{[(benzyloxy)imino]methyl}phenyl)acrylic acid (ST3076) for the synthesis of ST2840 was obtained (0.54 g, 98%) as described in step 1, example 1, starting from trans 4-formyl-cinnamic acid A (0.348 g, 1.97 mmol) and B O-benzylhydroxylamine hydrochloride (0.378.2 g, 2.36 mmol).

MS (ESI) m/z: $[M-1]^-$=280.3

$^1$H-NMR (200 MHz, DMSO-d$_6$) δ (ppm): 5.19 (s, 2H, CH$_2$—O); 6.58 (d, 1H, CH=C, J=16.1 Hz); 7.30-7.46 (m, 5H, 5×CH$_{ar}$); 7.59 (d, 1H, CH=C, J=15.7 Hz); 7.64 (d, 2H, 2×CH$_{ar}$); 7.74 (d, 2H, 2×CH$_{ar}$); 8.34 (s, 1H, CH=N).

$^{13}$C-NMR (50 MHz, DMSO-d$_6$) δ (ppm): 76.4; 121.0; 128.0; 128.6; 129.0; 129.1; 129.4; 134.1; 136.4; 138.2; 143.7; 149.5; 168.2.

Step 2. Compound ST2840 was obtained (0.080 mg, 75% yield) as described in step 2, example 1, starting from intermediate C (0.100 g, 0.36 mmol).

MS (ESI) m/z: $[M-1]^-$=295.2

$[M+23]^+$=319.1.

$^1$H-NMR (300 MHz, DMSO-d$_6$) δ (ppm): 5.18 (s, 2H, CH$_2$—O); 6.50 (d, J=15.78 Hz, 1H, CH=C,); 7.30-7.50 (m, 6H, 5×CH$_{ar}$+CH=C); 7.61 (m, 4H, 4×CH$_{ar}$); 8.32 (s, 1H, CH=N).

$^{13}$C-NMR (75.5 MHz, DMSO-d$_6$) δ (ppm): 76.3; 120.8; 128.1 128.6; 128.6; 128.9; 129.0; 133.4; 137.0; 138.1; 138.2; 149.5; 163.1.

Example 9

Preparation of (2E)-N-hydroxy-3-(4-{[(4-chlorobenzoyl)hydrazono]-methyl}phenyl)acrylamide (ST2888)

Step 1. Intermediate C (2E)-3-(4-{[(4-chlorobenzoyl)hydrazono]-methyl}phenyl)acrylic acid for the synthesis of ST2888 was obtained (0.255 g, 78%) as described in step 1, example 1, starting from trans 4-formyl-cinnamic acid A (0.176 g, 1.00 mmol) and B 4-Chlorobenzoic Hydrazide (0.170 g, 1.00 mmol) in 2 mL of EtOH at reflux with 5% v/v HCl (37%). After 5 h stirring, the reaction was cooled at room temperature, filtered and the solid was washed with EtOH.

MS (ESI) m/z: $[M-1]^-$=327.2.

Step 2. Compound ST2888 was obtained (0.110 g, 53% yield) as described in step 2, example 1, starting from intermediate C (0.200 g, 0.61 mmol).

MS (ESI) m/z: $[M+23]^+$=366.3

$[M-1]^-$=342.1

$^1$H-NMR (200 MHz, DMSO-d$_6$) δ (ppm): 6.51 (d, J=15.9 Hz, 1H, CH=C); 7.46 (d, J=15.8 Hz, 1H, CH=C); 7.61 (t, 4H, 4×CH$_{ar}$); 7.75 (d, 2H, 2×CH$_{ar}$); 7.92 (d, 2H, 2×CH$_{ar}$); 8.43 (s, 1H, CH=N); 11.95 (s, 1H, NH).

$^{13}$C-NMR (50 MHz, DMSO-d$_6$) δ (ppm): 120.8; 128.3; 128.6; 129.3; 130.3; 132.8; 135.8; 137.2; 137.3; 138.2; 148.1; 162.9; 163.5.

Example 10

Preparation of (2E)-N-(2-aminophenyl)-3-[4-({[(4-nitrobenzyl)oxy]imino}-methyl)phenyl]-acrylamide (ST3070)

Step 1: synthesis of intermediate C (2E)-3-[4-({[(4-nitrobenzyl)oxy]imino}methyl)phenyl]acrylic acid was described in step 1, example 3.

Step 2: compound ST3070 was obtained (0.12 g, 60% yield) dissolving intermediate C (0.158 g, 0.48 mmol), PyBOP (0.276 g, 0.53 mmol), DIEA (252 μL, 1.45 mmol) in 3 mL of DMF and this solution was added slowly to a solution of o-phenylendiamine (0.261 g, 2.42 mmol) in 0.5 mL of DMF. When reaction ended, DMF was distilled under reduced pressure and crude product was purified by flash chromatography on silica gel (eluent CH$_2$Cl$_2$/Dioxane=95/5).

MS (ESI) m/z: $[M+1]^+$=417.1

$^1$H-NMR (200 MHz, DMSO-d6) δ (ppm): 4.98 (bs, 2H, NH$_2$), 5.36 (s, 2H, CH$_2$), 6.5-6.6 (t, J=7.3 Hz, 1H, CH$_{ar}$), 6.7-6.8 (d, J=7.6 Hz, 1H, CH$_{ar}$), 6.9-7.0 (m, 2H, CH, CH$_{ar}$), 7.3-7.4 (d, 1H, J=7.7 Hz, CH$_{ar}$), 7.5-7.7 (d, J=15.8 Hz, 1H, CH) 7.67 (m, 6H, 6×CH$_{ar}$), 8.2-8.3 (d, J=8.2 Hz, 2H, 2×CH$_{ar}$), 8.43 (s, 1H, CH), 9.43 (bs, 1H, NH).

$^{13}$C-NMR (50 MHz, DMSO-d6) δ (ppm): 67.1, 74.9, 116.7, 117.0, 124.1, 124.3, 125.5, 126.6, 128.3, 128.8, 129.5, 133.3, 137.3, 139.4, 142.4, 146.6, 147.7, 150.4, 164.0.

Example 11

Preparation of (2E)-N-hydroxy-3-(1H-indol-5-yl)acrylamide (ST2880)

For the preparation of this compound the general Scheme II was followed (see also Kato, K.; Ohkawa, S.; Terao, S.; Terashita, A. I.; Nishikawa, K. *J. Med. Chem.* 1985, 28, 287 and Pindur, U.; Pfeuffer, L. *Monatsh. Chem.* 1989, 120, 157.

Step 1. A solution of 1H-indole-5-carbaldehyde (0.217 g, 1.5 mmol) and methyl (triphenylphosphoranylidene)acetate (0.535 g. 1.6 mmol) in DCM (4 mL) was stirred in a flask under reflux overnight, then the solvent was removed under reduced pressure. Purification by silica gel column chromatography, with a mixture of DCM/Hexane 8:2 as eluent system, gave 0.291 g of methyl (2E)-3-(1H-indol-5-yl)acrylate (97% yield).

MS (ESI) m/z: $[M-1]^-$=200.2

$[M+23]^+$=224.2.

¹H-NMR (200 MHz, CDCl₃) δ (ppm): 6.46 (d, 1H, CH=C, J=15.8 Hz); 6.62 (m, 1H, CH$_{ar}$); 7.26 (m, 1H, CH$_{ar}$); 7.43 (m, 2H, CH$_{ar}$); 7.83-7.93 (m, 2H, CH$_{ar}$+CH=C); 8.41 (s, 1H, NH).

¹³C-NMR (50 MHz, CDCl₃) δ (ppm): 51.63; 103.61; 111.68; 114.73; 121.70; 122.50; 125.41; 126.64; 128.27; 137.14; 146.84; 168.24.

Step 2. To a solution of intermediate methyl (2E)-3-(1H-indol-5-yl)acrylate obtained from step 1 (255 mg, 1.27 mmol) in MeOH/H₂O 5:1 (10 mL) was added solid LiOH (532 mg, 12.7 mmol) and the reaction mixture was stirred at room temperature overnight. The solution was acidified (pH ~1) with HCl 1N and then extracted with ethyl acetate. The organic layer was washed with H₂O (×3), then dried over sodium sulfate, filtered and evaporated under reduced pressure to give 0.24 g of intermediate E (2E)-3-(1H-indol-5-yl) acrylic acid (94% yield).

MS (ESI) m/z: [M−1]⁻=186.0
[M+23]⁺=210.1.

Step 3. In a flask hydroxylamine hydrochloride (0.379 g mg, 5.45 mmol) and DBU (830 mg, 5.45 mmol) were dissolved in DMF (0.5 mL) and the resulting solution was added to a suspension of intermediate E (0.507 g, 2.726 mmol), HATU (1.04 g, 2.726 mmol) and DIEA (1.19 mL, 6.81 mmol) in DMF (2 mL). When reaction ended, mixture was concentrated under reduced pressure and the residue was purified by preparative RP-HPLC (column Lichrosorb RP-18, 7 μm; eluents: H₂O/CH₃CN 60:40; flow=10 mL/min) to give the product F ST2880 (0.165 g, 30%).

MS (ESI) m/z: [M−H]⁻=200.9
[M+23]⁺=224.9

¹H-NMR (300 MHz, DMSO-d₆) δ (ppm): 6.35 (d, 1H, CH=C, J=15.7 Hz); 6.46 (br, 1H, CH$_{ar}$); 7.28-7.44 (m, 3H, CH$_{ar}$); 7.53 (d, 1H, CH=C, J=15.7 Hz); 7.72 (s, 1H, CH$_{ar}$); 11.25 (s, 1H, NH).

¹³C-NMR (75.5 MHz, DMSO-d₆) δ (ppm): 102.52; 112.66; 115.93; 120.68; 121.67; 126.61; 127.09; 128.58; 137.33; 141.02; 164.27.

Example 12

Preparation of (2E)-N-hydroxy-3-{3-[(2-morpholin-4-ylethoxyimino)methyl]-phenyl}-acryl-amide hydrochloride (ST3576)

Step 1. Intermediate C (2E)-3-(3-{(E)-[(2-morpholin-4-ylethoxy)imino]methyl}-phenyl)acrylic acid for the synthesis of ST3576 was obtained (1.232 g, 98%) as described in step 1, example 1, starting from trans 3-formyl-cinnamic acid A (Y=CH=CH, R₁=H, R₃=H, 0.650 g, 3.69 mmol) and B 2-(2-morpholin-4-yl)-O-ethylhydroxylamine dihydrochloride (0.808 g, 3.69 mmol).

MS (ESI) m/z: [M+1]⁻=305.1 trans 3-formyl-cinnamic acid A (0.699 g, 3.97 mmol, 92% yield) was previously obtained by basic hydrolysis (excess of NaOH in EtOH/water=1/1) of methyl (2E)-3-(3-formylphenyl)acrylate obtained by reaction of 3-iodobenzaldehyde (1.000 g, 4.31 mmol) with methyl acrylate (775 μL, 8.62 mmol), NaHCO₃ (0.905 g, 10.75 mmol), nBU₄NCl (1.200 g, 4.31 mmol) and Pd(OAc)₂ (0.019, 0.09 mmol) in DMF (6 mL).

Step 2. Compound ST3576 was obtained (0.931 mg, 98% yield) after acid hydrolysis of (2E)-3-{3-[(2-Morpholin-4-yl-ethoxyimino)-methyl]-phenyl}-N-trityloxy-acrylamide obtained (1.500 g, 2.67 mmol, 65% yield) by reaction of intermediate C (1.400 g, 4.12 mmol) with ethyl chloroformate (472 μL, 4.94 mmol) and TEA (746 μL, 5.35 mmol) in 5 mL of anhydrous THF (according to procedure described in Mai A., Pezzi R. et all. *J. Med. Chem.* 2005, 48, 3344 and in Mai A., Pezzi R. et all. *J. Med. Chem.* 2003, 46, 4826).

MS (ESI) m/z: [M+1]⁻=320.1
[M−1]⁻=318.1

¹H-NMR (300 MHz, CD₃OD, δ): 3.30-3.22 (m, 2H, CH₂), 3.54-3.64 (m, 4H, 2×CH₂), 3.85 (t, J=11.4 Hz, 2H, CH₂), 4.03-4.10 (m, 2H, CH₂), 4.54-4.90 (m, 2H, CH₂); 6.40-6.60 (d, J=15.6 Hz, 1H, CH=C,); 7.40-7.50 (t, J=7.5 Hz, 1H, CH$_{ar}$), 7.50-7.70 (m, 4H, 3×CH$_{ar}$+CH=C); 7.79 (s, 1H, CH$_{ar}$); 8.27 (s, 1H, CH=N).

¹³C-NMR (75.5 MHz, CD₃OD, δ): 52.6, 56.2; 63.7; 67.6; 118.3; 126.6; 128.2; 129.0; 129.3; 132.6; 135.7; 139.6; 150.6; 164.7.

Example 13

Preparation of N-hydroxy-3-[4-({[(4-nitrobenzyl)oxy]imino}methyl)phenyl]propanamide (ST3330)

Step 1. Intermediate C₃-[4-({[(4-nitrobenzyl)oxy]imino}-methyl)phenyl]propanoic acid for the synthesis of ST3330 was obtained (0.230 g, 78%) as described in step 1, example 1, starting from 3-(4-formylphenyl)propanoic acid A (Y=CH₂—CH₂, R₁=H, R₃=H 0.160 g, 0.90 mmol) and B O-(4-Nitrobenzyl)hydroxylamine hydrochloride (0.202 g, 0.99 mmol).

MS (ESI) m/z: [M+23]⁻=351.1.

3-(4-formylphenyl)propanoic acid A (Y=CH₂—CH₂, R₁=H, R₃=H 0.160 g, 0.90 mmol) was obtained after basic hydrolysis (excess LiOH in 1/1 water/THF solution) of ethyl 3-(4-formylphenyl)propanoate as crude product obtained by reaction of 4-bromobenzaldehyde (0.160 mg, 0.86 mmol) with acrolein diethyl acetal (396 μL, 2.60 mmol) in presence of Bu₃N (412 μL, 1.73 mmol), Bu₄NCl (0.240 g, 0.86 mmol) and Pd(OAc)₂ (0.006 g, 0.03 mmol) in DMF at 90° C. overnight (according to procedure described in Battistuzzi G., Cacchi S., Fabrizi G., Bernini R. *Synlett,* 2003, 8, 1133).

Step 2. Compound ST3330 was obtained (0.030 g, 95% yield) after acid hydrolysis of 3-{4-[(4-nitro-benzyloxy-imino)-methyl]-phenyl}-N-trityloxy-propanamide obtained (0.054 g, 0.09 mmol, 60% yield) by reaction of intermediate C₃-[4-({[(4-nitrobenzyl)oxy]imino}-methyl)phenyl]propanoic acid (0.050 g, 0.15 mmol) with HATU (0.064 g, 0.17 mmol), TEA (43 μL, 0.31 mmol) and o-tritylhydroxylamine (0.048 g, 0.17 mmol) in DMF at room temperature.

MS (ESI) m/z: [M+23]⁺=366.2
[M−1]⁻=342.2

¹H-NMR (300 MHz, DMSO-d₆) δ (ppm): 2.23 (t, J=7.6 Hz, 2H, CH₂), 2.80 (t, J=7.6 Hz, 2H, CH₂), 5.29 (s, 2H, CH₂), 7.20-7.24 (d, J=7.94 Hz, 2H, 2×CH$_{ar}$), 7.47-7.50 (d, J=8.1 Hz, 2H, 2×CH$_{ar}$), 7.62-7.66 (d, J=8.7 Hz, 2H, 2×CH$_{ar}$), 8.20-8.24 (d, J=8.8 Hz, 2H, 2×CH$_{ar}$), 8.32 (s, 1H, CH), 8.70 (bs, 1H, NH), 10.30 (bs, 1H, OH).

¹³C-NMR (75.5 MHz, DMSO-d₆) δ (ppm): 168.7, 150.6, 147.6, 146.6, 144.2, 130.1, 129.4, 129.3, 127.7, 124.2, 74.6, 34.2, 31.4.

Example 14

Preparation of (2E)-N-(2-Amino-phenyl)-3-{4-[(2-morpholin-4-yl-ethoxyimino)methyl]-phenyl}-acrylamide hydrochloride (ST3573)

Step 1: synthesis of intermediate C (2E)-3-(4-{(E)-[(2-morpholin-4-ylethoxy)imino]methyl}-phenyl)acrylic acid was described in step 1, example 7.

Step 2: (2E)-N-(2-Amino-phenyl)-3-{4-[(2-morpholin-4-yl-ethoxyimino)methyl]-phenyl}-acrylamide obtained (0.740 g, 57% yield) was obtained by reaction of intermediate C (1.000 g, 3.28 mmol), HATU (1.370 g, 3.61 mmol), TEA (550 μL, 3.90 mmol) in 9 mL of $CH_2Cl_2$; this solution was added slowly to a solution of o-phenylendiamine (0.370 g, 3.45 mmol) in 1 mL of $CH_2Cl_2$. When reaction ended, $CH_2Cl_2$ was distilled under reduced pressure and crude product was purified by flash chromatography on silica gel (eluent $CH_2Cl_2/CH_3OH$/n-Hexane/TEA=67/2/29/2).

MS (ESI) m/z: $[M+1]^+$=394.9

$^1$H-NMR (500 MHz, DMSO-d6, δ): 2.48 (m, 4H, 2×$CH_2$), 2.64 (t, J=5.8 Hz, 2H, $CH_2$), 3.58 (t, J=5.0 Hz, 4H, 2×$CH_2$), 4.26 (t, J=5.7 Hz, 2H, $CH_2$), 4.92 (bs, 2H, $NH_2$), 6.5-6.6 (t, J=8.1 Hz, 1H, $CH_{ar}$), 6.7-6.8 (d, J=7.6 Hz, 1H, $CH_{ar}$), 6.9-7.0 (d, J=15.7 Hz, 1H, CH), 6.9-7.0 (t, J=8.1 Hz, 1H, $CH_{ar}$), 7.3-7.4 (d, 1H, J=7.7 Hz, $CH_{ar}$), 7.5-7.6 (d, J=15.4 Hz, 1H, CH), 7.6-7.7 (m, 4H, 4×$CH_{ar}$), 8.29 (s, 1H, CH), 9.41 (s, 1H, NH).

$^{13}$C-NMR (126 MHz, DMSO-d6, δ): 54.3, 57.6, 66.9, 72.2, 116.7, 117.0, 124.0, 124.2, 125.4, 126.5, 128.1, 128.8, 133.7, 137.0, 139.5, 142.3, 149.0, 164.0. Compound ST3573 was obtained (0.660 g, 1.69 mmol, 90% yield) after acidification with HCl 4.0 M in Dioxane of (2E)-N-(2-Amino-phenyl)-3-{4-[(2-morpholin-4-yl-ethoxyimino)methyl]-phenyl}-acrylamide (0.740 g, 1.88 mmol).

Example 15

Preparation of (2E)-N-Mercapto-3-{4-[(4-nitro-benzyloxyimino)-methyl]-phenyl}-acrylamide (ST3605)

Step 1. synthesis of intermediate C (2E)-3-[4-({[(4-nitrobenzyl)oxy]imino}-methyl)phenyl]acrylic acid (ST3075) was described in step 1, example 3.

Step 2. Compound (2E)-3-{4-[(4-Nitro-benzyloxyimino)-methyl]-phenyl}-N-tritylsulfanyl-acrylamide was obtained (0.050 g, 0.08 mmol, 26% yield) by reaction of intermediate C (2E)-3-[4-({[(4-nitrobenzyl)oxy]imino}-methyl)phenyl]acrylic acid (ST3075, 0.100 g, 0.31 mmol) with $SOCl_2$ (34 μL, 0.46 mmol), DIEA (236 μL, 1.38 mmol) and Triphenylmethanesulfenamide (0.098 g, 0.14 mmol) in anhydrous DCM at room temperature.

MS (ESI) m/z: $[M+1]^+$=600.7

$[M+23]^+$=622.1

$[2M+1]^+$=1199.4

$^1$H-NMR (300 MHz, DMSO-$d_6$) δ (ppm): 5.32 (s, 2H, $CH_2$), 6.50-6.60 (d, J=16.0 Hz, 1H, CH=C,); 7.20-7.40 (m, 18H, 17×$CH_{ar}$+CH=C); 7.55-7.65 (d, J=7.7 Hz, 2H, 2×$CH_{ar}$); 7.60-7.70 (d, J=8.7 Hz, 2H, 2×$CH_{ar}$); 8.20-8.30 (d, J=8.7 Hz, 2H, 2×$CH_{ar}$) 8.38 (s, 1H, $CH_{ar}$); 8.96 (s, 1H, NH).

$^{13}$C-NMR (75.5 MHz, DMSO-$d_6$) δ (ppm): 57.8, 74.9, 124.2, 127.8, 128.1, 128.6, 128.9, 129.2; 129.4; 130.2; 133.4; 136.8; 140.5; 143.6; 146.5; 147.7; 150.3; 154.4.

Compound ST3605 was obtained (0.006 g, 20% yield) after non optimized-deprotection of (2E)-3-{4-[(4-Nitrobenzyloxyimino)-methyl]-phenyl}-N-tritylsulfanyl-acrylamide.

MS (ESI) m/z: $[M-1]^-$=356.2

Example 16

Preparation of N-hydroxy-3-{4-[(E)-{[(4-nitrobenzyl)oxy]imino}methyl]phenyl}-prop-2-ynamide (ST3618)

ST3618 synthesis can be achieved according to general Scheme I, by preparation of corresponding intermediate C (3-[4-({[(4-nitrobenzyl)oxy]imino}-methyl)phenyl]propiolic acid) starting from p-formylphenylpropiolic acid A. This intermediate can be obtained by reaction of 4-iodobenzaldehyde with propriolic acid in presence of a Pd-catalyst. Because of low yields, however, and of subsequent formation of hydroxamate group starting from methyl ester, it's better to synthesize directly methyl 3-(4-formylphenyl)propiolate as intermediate (according to procedure described in Eckert T. and Ipaktschi R. in *Synt Comm*. 1998, 28, 327).

Step 1. Methyl 3-[4-({[(4-nitrobenzyl)oxy]imino}-methyl)phenyl]propiolate for the synthesis of ST3618 was obtained (0.325 g, 96%) as described in step 1, example 1, starting from methyl 3-(4-formylphenyl)propiolate (0.180 g, 1.00 mmol) and B O-(4-Nitrobenzyl)hydroxylamine hydrochloride (0.202 g, 1.00 mmol).

Methyl 3-(4-formylphenyl)propiolate (0.460 g, 2.43 mmol, 80% yield) was obtained by reaction of 4-iodobenzaldehyde (0.700 mg, 3.02 mmol) with methylpropionate (1.013 g, 12.06 mmol) in presence of $K_2CO_3$ (0.846 g, 6.04 mmol), CuI (0.022 g, 0.12 mmol) and $Pd(PPh_3)_2Cl_2$ (0.042 g, 0.06 mmol) in THF at 65° C. Then 12 h the THF was evaporated at vacuum and the residual was extracted with $Et_2O/H_2O$. The crude products were purified by silica gel column chromatography.

Step 2. Compound ST3618 was obtained (0.007 g, 60% yield) after acid hydrolysis of 3-{4-[(4-nitro-benzyloxyimino)-methyl]-phenyl}-N-tetrahydropyranyl-propiolamide obtained (0.150 g, 0.44 mmol, 35% yield) by reaction of methyl 3-[4-({[(4-nitrobenzyl)oxy]imino}-methyl)phenyl]propiolate (0.150 g, 0.44 mmol) with bis-(trimethylsilyl)-natriumamid 1.0M in THF (1.0 mL, 0.44 mmol), and O-tetrahydropyranylhydroxylamine (0.052 g, 0.44 mmol) in THF at −78° C. for 2 h.

MS (ESI) m/z: $[M+1]^+$=340.0

$[M-1]^-$=338.1

$^1$H-NMR (500 MHz, $CD_3OD$) δ (ppm): 5.35 (s, 2H, $CH_2$), 7.58-7.60 (d, J=8.5 Hz, 2H, 2×$CH_{ar}$), 7.64-7.69 (m, 4H, 4×$CH_{ar}$), 8.24-8.27 (d, J=8.5 Hz, 2H, 2×$CH_{ar}$), 8.29 (s, 1H, CH).

$^{13}$C-NMR (125.7 MHz, $CD_3OD$) δ (ppm): 152.0, 149.0, 147.8, 145.9, 134.1, 132.6, 128.6, 127.2, 123.4, 121.6, 86.0, 81.3, 74.9.

LIST OF ABBREVIATIONS

AcCN Acetonitrile

AcOEt Ethyl Acetate

DBU 1,8-Diazabicyclo[5.4.0]undec-7-ene

DCC Dicycloexylcarbodiimide

DCM Dichloromethane

DIEA N,N, N-diisopropylethylamine

DMAP 4-Dimethylaminopyridine

DMF Dimethylformamide

DMSO Dimethylsulfoxide

HOBt Hydroxybenzotriazole

MeOH Methanol

NMM N-Methylmorpholine

RP-HPLC Reversed Phase-HPLC

TEA Triethylamine

TFA trifluoroacetic acid

THF Tetrahydrofuran

Biological Results

Cytotoxicity Studies

To test the effects of the compounds on cell growth, NB4 human promyelocytic leukaemia, NCI-H460 non-small cell carcinoma cells and HCT-116 human colon carcinoma cells were used. NB4 and NCI-H460 tumour cells were grown RPMI 1640 containing 10% fetal bovine serum (GIBCO), whereas HCT-116 tumour cells were grown in McCoy's 5A containing 10% fetal bovine serum (GIBCO).

Tumour cells were seeded in 96-well tissue culture plates (Corning) at approximately 10% confluence and were allowed to attach and recover for at least 24 h. Varying concentrations of the drugs were then added to each well to calculate their IC50 value (the concentration which inhibits the 50% of cell survival). The plates were incubated for 24 h at 37° C. At the end of the treatment, for NB4 tumour cells in suspension, the procedure was performed as follows: medium culture was removed by centrifugation of the plates at 1600×g for 10 min and the surnatant was removed. 250 µl PBS were added, then the plates were centrifuged at 1600×g for 10 min, the surnatant was removed. 200 µl/well of medium culture RPMI 1640 containing 10% FCS were added and the plates were incubated at 37° C. for other 48 h. The plates were centrifuged again at 1600×g for 10 min, the medium culture was removed and 200 µl PBS and 50 µl of cold 80% TCA were added. The plates were incubated on ice for at least 1 h. TCA was removed, the plates were washed 3 times for immersion in distilled-water and dried on paper and at 40° C. for 5 min. Then 200 µl of 0.4% sulphorodamine B in 1% acetic acid were added. The plates were incubated at room temperature for other 30 min. Sulphorodamine B was removed, the plates were washed for immersion in 1% acetic acid for 3 times, then they were dried on paper and at 40° C. for 5 min. Then 200 µl Tris 10 mM were added, the plates were kept under stirring for 20 min. The survival cell was determined as optical density by a Multiskan spectrofluorimeter at 540 nm. For the tumour cells in adhesion (NCI-H460 and HCT-116), the procedure was as above mentioned, except that at the end of the treatment, the plates were washed by remotion of the surnatant and addition of PBS 3 times without centrifugation. Also the last day of the assay, the surnatant was removed without centrifugation.

The amount of cells killed was calculated as the percentage decrease in sulphorodamine B binding compared with control cultures. The $IC_{50}$ values (the concentration which inhibits the 50% of cell survival) were calculated with the "ALLFIT" program. In the table 1 the cytotoxicity evaluated on NB4 tumour cells showed that some compounds (ST2840, ST2986, ST2987, ST3049, ST2888) were the most potent since IC50 values ranged from 0.6 to 0.8 µM. The molecules ST2984, ST3050, ST2880, ST3330, ST3576 followed by ST2985 and ST2983 were slightly less efficacious (IC50 values ranged from 1.4 to 2.9 µM). With regards to the effect on survival of NCI-H460 tumour cells, all the compounds were less potent than on NB4 tumour cells (IC50 ranged from 1.6 to 7.7 µM). In this case, the molecules showing a minor cytotoxic effect were ST2985, ST2983, ST3330, ST3576 and ST2880. On HCT-116 the cytotoxicity of the compounds mentioned before was comparable (IC50=1.2-4.0 µM). With regards to ST3070, ST3075 and ST3076, ST3573 the compounds revealed a minor inhibiting action on survival cells, because IC50 calculated on NB4, NCl-H460 and HCT-116 ranged from 8.9 µM to 20 µM.

TABLE 1

Cytotoxicity of different compounds on NB4, NCI-H460 and HCT-116 tumour cells

| Compound | NB4 | NCI-H460 | HCT-116 |
|---|---|---|---|
| | | IC50 ± SD, µM | |
| ST2840 | 0.6 ± 0.006 | 1.6 ± 0.1 | 2.8 ± 0.2 |
| ST2880 | 1.8 ± 0.02 | 5.9 ± 0.5 | 2.7 ± 0.3 |
| ST2888 | 0.8 ± 0.02 | 3.4 ± 0.3 | 1.8 ± 0.1 |
| ST2983 | 2.9 ± 0.1 | 6.3 ± 0.4 | 3.5 ± 0.3 |
| ST2984 | 1.4 ± 0.07 | 3.2 ± 0.09 | 3.5 ± 0.07 |
| ST2985 | 2.7 ± 0.09 | 5.1 ± 0.3 | 3.7 ± 0.4 |
| ST2986 | 0.7 ± 0.07 | 1.6 ± 0.07 | 2.4 ± 0.1 |
| ST2987 | 0.8 ± 0.01 | 2.6 ± 0.1 | 1.2 ± 0.2 |
| ST3049 | 0.8 ± 0.09 | 1.7 ± 0.1 | 1.7 ± 0.1 |
| ST3050 | 1.7 ± 0.2 | 2.9 ± 0.4 | 1.8 ± 0.1 |
| ST3070 | >20 | 200 | 33.4 ± 3.9 |
| ST3075 | >20 | 21.3 ± 3.0 | >20 |
| ST3076 | >20 | 17.9 ± 2.0 | >20 |
| ST3330 | 0.95 ± 0.06 | 7.7 ± 1.0 | 3.1 ± 0.1 |
| ST3573 | 8.87 ± 0.6 | >20 | >20 |
| ST3576 | 1.89 ± 0.08 | 6.6 ± 0.8 | 4.0 ± 0.5 |

The invention claimed is:

1. A compound of the following formula I:

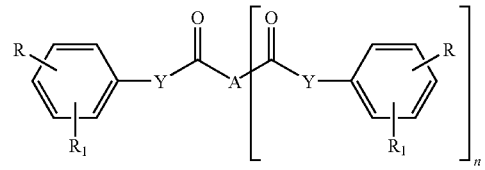

[FORMULA I]

wherein:

n is 0;

A is a monovalent group and is selected from the group consisting of: NH—OG and, the group

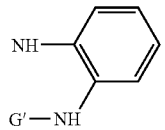

where G and G' are H,

Y is a group selected among HC=CH, $CH_2$—$CH_2$ and C≡C;

R is the group:

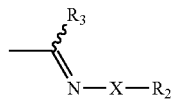

where X is either O, NH;

or

R is the group:

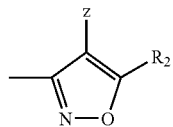

Z is H;

$R_1$ is H;

or:

R and $R_1$, taken together with the aromatic group, form a polycyclic group having the following formula:

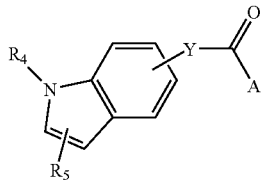

$R_2$ is selected from the group consisting of:
- H;
- $(C_6-C_{12})$ aryl or $(C_6-C_{12})$ aryl substituted with nitro, halogen, $(C_1-C_4)$ alkoxycarbonyl;
- $(C_1-C_4)$ alkyl, $(C_2-C_4)$ alkenyl;
- $(C_6-C_{12})$ aryl-$(CH_2)_{n''}$, where aryl is substituted with nitro halogen, $(C_1-C_4)$ alkoxycarbonyl, where n''=0-3;
- $(C_6-C_{12})$ aryl-CO, where aryl is substituted with halogen $(C_1-C_4)$; and
- $(C_6)$ heterocyclyl-$(C_1-C_3)$ alkylene where at least one of the $CH_2$ of the heterocycle is substituted by O;

$R_3$ is H;
$R_4$ is H;
$R_5$ is H;

its tautomers, geometrical isomers, optically active forms as enantiomers, diastereomers and racemate forms, as well as its pharmaceutically acceptable salts.

2. The compound according to claim 1, wherein Y is the group HC=CH.

3. The compound according to claim 1, wherein $R_2$ is selected from the group consisting of: $R_2$ is selected from the group consisting of: H; —$(C_6-C_{12})$ aryl; —$(C_6-C_{12})$ aryl-$(CH_2)_n$ where aryl is substituted with nitro, halogen, $C_1-C_4$ alkoxycarbonyl; —$(C_6-C_{12})$ aryl-CO; and $(C_3-C_6)$ heterocyclyl-$(C_1-C_3)$ alkylene, where at least one of the $CH_2$ of the heterocycle is substituted by NH.

4. The compound of Formula (I) of claim 1, which is selected from the group consisting of:
- (2E)-N-hydroxy-3-(4-{[(allyloxy)imino]methyl}phenyl)acrylamide;
- (2E)-N-hydroxy-3-{4-[(phenoxyimino)methyl]phenyl}acrylamide;
- (2E)-N-hydroxy-3-[4-({[(4-nitrobenzyl)oxy]imino}-methyl)phenyl]acrylamide;
- (2E)-N-hydroxy-3-{4-[(hydroxyimino)methyl]phenyl}acrylamide;
- (2E)-N-hydroxy-3-[4-({[(pentafluorobenzyl)oxy]imino}-methyl)pheny]-acrylamide;
- (2E)-N-hydroxy-3-[4-({[(4-methoxycarbonylbenzyl)oxy]imino}-methyl)phenyl]-acrylamide;
- (2E)-N-hydroxy-3-{4-[(2-morpholin-4-ylethoxyimino)methyl]-phenyl}-acrylamide;
- (2E)-3-(4-{[(benzyloxy)imino]methyl}phenyl)-N-hydroxyacrylamide;
- (2E)-N-hydroxy-3-(4-{[(4-chlorobenzoyl)hydrazono]-methyl}phenyl)acrylamide;
- (2E)-N-(2-aminophenyl)-3-[4-({[(4-nitrobenzyl)oxy]imino}-methyl)phenyl]-acrylamide;
- (2E)-N-hydroxy-3-(1H-indol-5-yl)acrylamide;
- (2E)-N-hydroxy-3-{3-[(2-morpholin-4-ylethoxyimino)methyl]-phenyl}-acryl-amide hydrochloride;
- N-hydroxy-3-[4-({[(4-nitrobenzyl)oxy]imino}-methyl)phenyl]propanamide; and
- (2E)-N-(2-Amino-phenyl)-3-{4-[(2-morpholin-4-ylethoxyimino)methyl]-phenyl}-acrylamide hydrochloride.

5. A medicament comprising a compound according to claim 1.

6. A pharmaceutical composition containing as active ingredient a compound according to claim 1 and at least one pharmaceutically acceptable excipient and/or diluent.

7. The pharmaceutical composition according to claim 6 in combination with one or more known antitumor agents.

8. The pharmaceutical composition according to claim 7, in which the known antitumor agent is selected from the group consisting of alkylating agents, topoisomerase inhibitors, anti-tubulin agents, intercalating compounds, anti-metabolites, natural products such as vinca alkaloids, epipodophyllotoxins, antibiotics, enzymes, taxans, and cytodifferentiating compounds.

9. The composition according to claim 8, in which the cytodifferentiating antitumor compound is all-trans retinoic acid.

* * * * *